US009255880B2

(12) United States Patent
Murray

(10) Patent No.: US 9,255,880 B2
(45) Date of Patent: Feb. 9, 2016

(54) APPARATUS AND METHOD FOR EVALUATING POWER TRANSMISSION CONDUCTORS

(71) Applicant: Electric Power Research Institute, Inc., Charlotte, NC (US)

(72) Inventor: Neal Scott Murray, Charlotte, NC (US)

(73) Assignee: Electric Power Research Institute, Inc., Charlotte, NC (US)

( * ) Notice: Subject to any disclaimer, the term of this patent is extended or adjusted under 35 U.S.C. 154(b) by 0 days.

(21) Appl. No.: 14/143,069

(22) Filed: Dec. 30, 2013

(65) Prior Publication Data

US 2015/0185145 A1 Jul. 2, 2015

(51) Int. Cl.
  G01J 5/02 (2006.01)
  G01N 21/55 (2014.01)
  G01J 5/08 (2006.01)

(52) U.S. Cl.
  CPC .............. *G01N 21/55* (2013.01); *G01J 5/0853* (2013.01)

(58) Field of Classification Search
  CPC .................................................. G01N 21/3563
  USPC ....................................................... 250/339.11
  See application file for complete search history.

(56) References Cited

U.S. PATENT DOCUMENTS

| 4,985,622 A * | 1/1991 | Kessler et al. ................. 250/226 |
| 7,361,922 B2 * | 4/2008 | Kameyama et al. .......... 250/574 |
| 8,393,109 B2 * | 3/2013 | Gilmore .......................... 42/113 |
| 2006/0086902 A1 * | 4/2006 | Gelbwachs .............. 250/339.12 |
| 2007/0018104 A1 * | 1/2007 | Parvin et al. ............. 250/339.13 |
| 2011/0038507 A1 * | 2/2011 | Hager ............................ 382/100 |

* cited by examiner

*Primary Examiner* — David Porta
*Assistant Examiner* — Edwin Gunberg
(74) *Attorney, Agent, or Firm* — Trego, Hines & Ladenheim, PLLC; Brandon Trego

(57) ABSTRACT

An apparatus and method for evaluating power transmission conductors is disclosed. The apparatus is configured to evaluate a charged power transmission conductor at a distance and includes a telescope assembly configured to transmit light to the conductor and receive a reflected light, in response to the transmitted light, from the conductor. The apparatus further includes control electronics configured to analyze the reflected light and determine a ratio based on two pre-determined frequencies, wherein the ratio is correlated with levels of iron oxide corrosion to confirm the presence of oxides that have leached through strands of the conductor.

7 Claims, 5 Drawing Sheets

APPARATUS AND METHOD FOR EVALUATING POWER TRANSMISSION CONDUCTORS

BACKGROUND OF THE INVENTION

This application relates to the evaluation of power transmission conductors and, more particularly, to an apparatus and method for evaluating power transmission conductors.

Conductor life and reliability are of increasing concern to many utilities. Many thousands of miles of lines are now approaching an age in service that has been deemed to be an expected life (i.e., 50-70 years). As a result, core wire failures resulting in outages, property damage, and loss of revenue is now being experienced, and the consequences of such failure may be significant with widespread implications.

In many areas with environmentally benign conditions conductor life could be significantly longer, whereas in more aggressive environmental conditions (coastal areas, areas with significant industrial pollution, agricultural areas where fertilizers and pesticides are used, and areas with moderate to high annual precipitation) conductors may experience premature failures due to core corrosion. Corrosion of the core is a determinant for conductor life and the detection of this condition is difficult and expensive.

Condition assessment of power transmission conductors, such as aluminum conductor steel reinforced (ACSR) conductors, has traditionally been completed by removing a section of the conductor that is in service and performing a visual inspection on each individual strand. This often requires a power outage, a team of linemen, and a bucket truck with winches and cable cutters to remove the section. The loose ends are then spliced onto a length of new conductor and then tensioned back to the original specifications.

Accordingly, a cost-effective apparatus and method is needed to detect evidence of core wire corrosion to enable utilities to better assess conductor condition and remaining life, and plan for conductor replacements.

BRIEF SUMMARY OF THE INVENTION

These and other shortcomings of the prior art are addressed by the present invention, which provides an apparatus configured to evaluate a charged power transmission conductor at a distance. The apparatus includes a telescope assembly configured to transmit light to the conductor and receive a reflected light, in response to the transmitted light, from the conductor. Control electronics are configured to analyze the reflected light and determine a ratio based on two pre-determined frequencies, wherein the ratio is correlated with levels of iron oxide corrosion to confirm the presence of oxides that have leached through strands of the conductor.

According to one aspect of the invention, an apparatus configured to evaluate a charged power transmission conductor at a distance includes a telescope assembly configured to transmit light to the conductor and receive a reflected light, in response to the transmitted light, from the conductor, and control electronics connected to the telescope assembly and configured to analyze the reflected light and determine a ratio based on two pre-determined frequencies, wherein the ratio is correlated with levels of iron oxide corrosion to confirm the presence of oxides that have leached through strands of the conductor. The telescope assembly includes a telescope configured to receive the reflected light, a dichroic splitter for splitting the reflected light into first and second light signals, first and second photodectors configured to receive the first and second light signals, wherein the first photodector receives the first light signal and the second photodector receives the second light signal, and an infra-red laser and a red laser configured to transmit light through a collimating output lens to the conductor. The control electronics include first and second lock-in amplifiers configured to produce a near DC output signal, the first lock-in amplifier being connected to the first photodector and the second lock-in amplifier being connected to the second photodetector; first and second modulation controllers configured to modulate the infra-red and red lasers, the first modulation controller being connected to the infra-red laser and the second modulation controller being connected to the red laser; and a microprocessor connected to the first and second lock-in amplifiers and the first and second modulation controllers. The microprocessor is configured to control the apparatus and perform processing of the reflected light.

According to another aspect of the invention, a method of evaluating a charged power transmission conductor includes the steps of providing an apparatus having a telescope assembly and control electronics, aiming the telescope assembly at a conductor to be evaluated, using the telescope assembly to transmit a light signal to the conductor and receive a reflected light signal from the conductor, and using the control electronics to process the reflected light signal and determine a ratio that is correlated with levels of iron oxide corrosion to confirm the presence of oxides that have leached through strands of the conductor.

BRIEF DESCRIPTION OF THE INVENTION

The subject matter that is regarded as the invention may be best understood by reference to the following description taken in conjunction with the accompanying drawing figures in which.

DETAILED DESCRIPTION OF THE INVENTION

Figure 1:
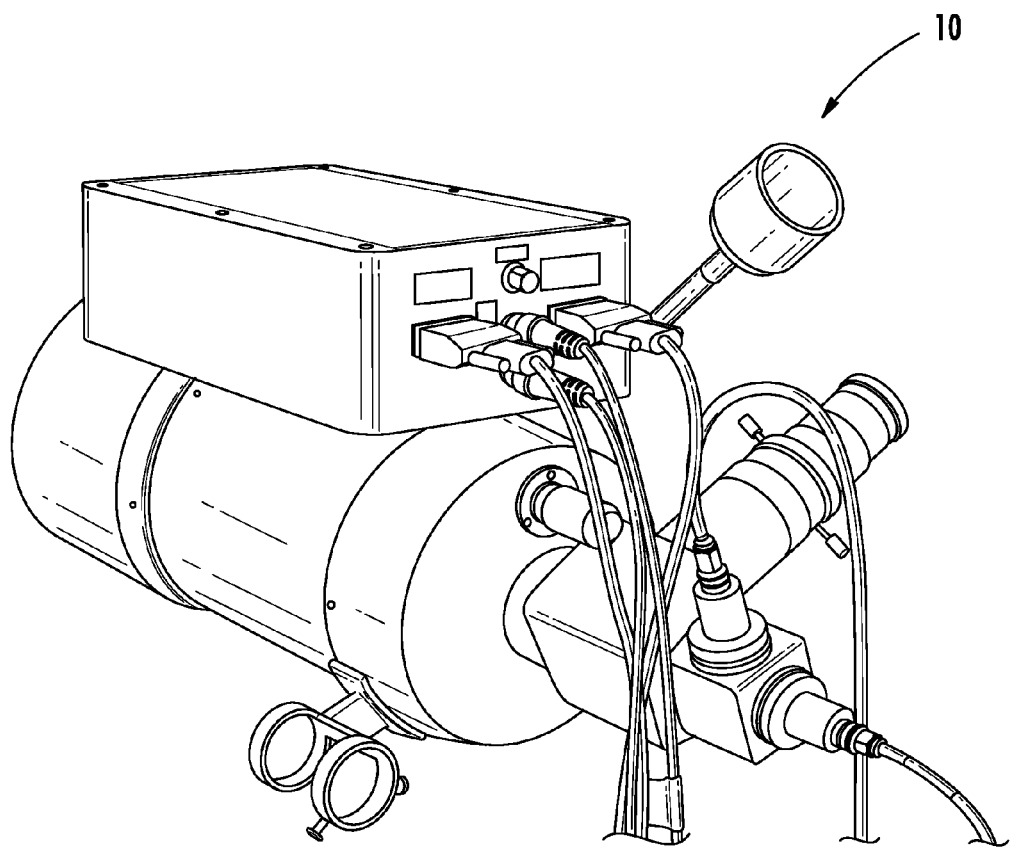
FIG. 1 illustrates an apparatus for evaluating power transmission conductors according to an embodiment of the invention.
Figure 2:
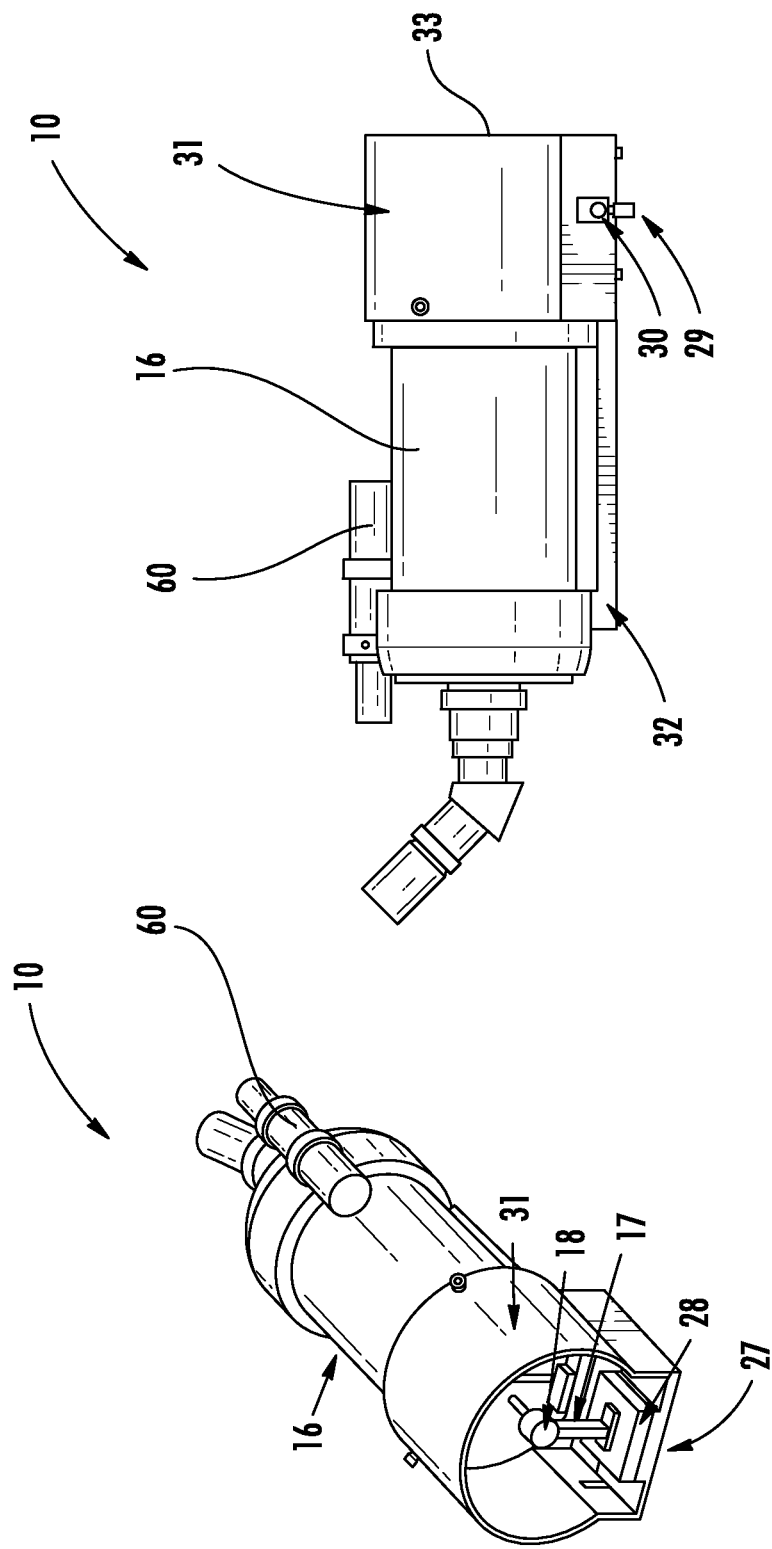
FIG. 2A is a perspective view of the apparatus of FIG. 1.
FIG. 2B is a side view of the apparatus of FIG. 1.
Figure 3:
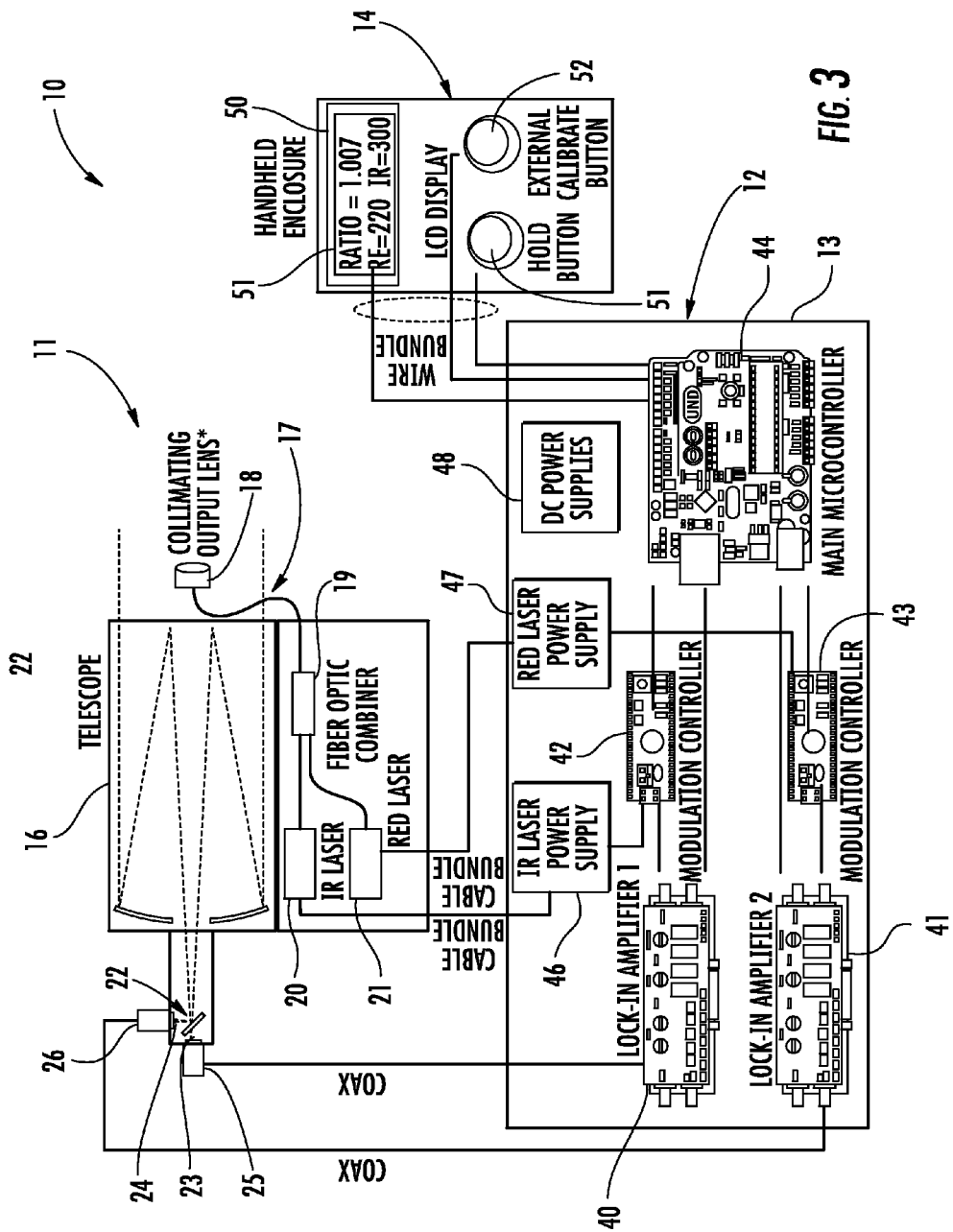
FIG. 3 is a schematic showing components of the apparatus of FIG. 1.

Referring to the drawings, an apparatus in accordance with an embodiment of the invention is illustrated in FIGS. 1-3 and shown generally at reference numeral 10. The apparatus 10 allows inspections to be performed without a system outage and can be completed from a distance with minimal time at the structure and minimal training requirements.

As shown, the apparatus 10 includes a telescope assembly 11, control electronics 12 contained in an external enclosure 13, and a handheld controller 14. The telescope assembly 11 includes a telescope 16 (a 5 inch telescope is shown—other suitable telescopes may be used), a fiber optic collimator 17 having a collimating output lens 18 connected by fiber optic cable to a fiber optic combiner 19 which is connected to an infra-red (IR) laser 20 operating at 830 nm and red laser 21 operating at 660 nm, a dichroic splitter 22, a pair of filters 23 and 24, and a pair of photo detectors 25 and 26 having photodiodes contained therein. The collimated light output is designed to create a spot several inches in diameter at a range of 100-200 ft.

As illustrated in FIGS. 2A and 2B, the fiber optic collimator 17 is mounted to the telescope 16 in a manner suitable for aligning and protecting the fiber optic collimator 17 as well as protecting the front of the telescope 16 while in use. The telescope 16 is used to collect the laser signal reflected from the target of interest. The laser signal is emitted from the collimator output lens 18, which is positioned in the center of the scope 16 at a distance of approximately 8 cm from the scope's 16 optics.

The collimator output lens 18 is rigidly secured in a two-part, collimator mount assembly 27. The collimator mount assembly 27 is secured to a pitch and yaw tilt platform 28 with pitch and yaw thumbscrew drives 29 and 30, respectively, for providing adjustments. Manual adjustment of the pitch and yaw drives 29, 30 allow a user of the apparatus 10 to fine-tune the alignment of the collimator output lens 18, and therefore laser beam direction. Both adjustment drives 29 and 30 have a travel range of ±4 degrees and a resolution of 10 arcsec and are easily accessible to a user positioned at the rear of the apparatus 10.

The pitch and yaw tilt platform 28 is secured to a two-part scope mount and shroud assembly 31 having a tripod attachment rail 32 and a shroud 33 which are rigidly secured to one another. The shroud 33 protects the collimator output lens from bumps or impacts during operation in the field.

Once the telescope 16 collects the laser signal reflected back from the target of interest, the signal is collected by detectors 25 and 26. As shown in FIG. 3, the signal/wavelengths are split into two signals by the dichroic splitter 22. The splitter 22 directs the two split signals to a respective one of the detectors 25 and 26. As shown, the signals are filtered by filters 23 and 24 prior to being detected by the detectors 25 and 26. The filters 23 and 24 remove ambient light which reduces photodiode shot noise by more than 100 times. Once the signals are collected by the detectors 25 and 26, the information from the detectors is sent to the control electronics 12 for processing. There are several advantages to this approach including allowing both lasers to be on continuously, adding the ability to narrowband filter the input and optimize the detection paths separately.

More particularly, light enters the telescope 16 and is split by the dichroic splitter 22 to transmit wavelengths longer than 750 nm while reflecting shorter wavelengths. Both optical paths are then filtered by the narrowband bandpass filters 23, 24 that are about 10 nm wide. Wavelengths outside of the passband of each filter 23, 24 are highly attenuated while the passbands are transmitted with about 85% efficiency. Finally, the optical paths terminated/collected by standard large area silicon photodiodes contained in the detectors 25 and 26. The length of the optical paths to each detector 25, 26 is set at the telescope's 16 focal plane. Table 1 shows an example list of equipment suitable for use in the telescope assembly.

TABLE 1

| Item | Manufacturer | Part Number | Description |
| --- | --- | --- | --- |
| Telescope | Celestron | C5 | 5", 1250 mm Schmidt Cassegrain Telescope |
| Flip Mirror Assembly | Orion | 05523 | 1.25" Astrophotography flip mirror |
| Dichroic Splitter | Edmund Optics | 69904 | 750 nm longpass, 25.2 × 35.6 mm |
| Bandpass Filter 660 | Edmund Optics | 86086 | 660 nm, 10 nm FWHM, 85% T, 12.5 mm diameter |
| Bandpass Filter 830 | Edmund Optics | 65119 | 830 nm, 10 nm FWHM, 85% T, 12.5 mm diameter |

TABLE 1-continued

| Item | Manufacturer | Part Number | Description |
| --- | --- | --- | --- |
| Photodiodes (x2) | Thorlabs | SM05PD1A | FDS100 mounted in SM05 tube, 3.6 × 3.6 mm |

The handheld controller 14 includes an enclosure 50 which contains an organic light-emitting diode (OLED) display 51 to show measured ratio and signal values, a calibration button 52 to activate a calibration mode and a hold button 53 to freeze the measurement display for easier data recording. The handheld controller 14 also includes a serial input rather than a parallel input to reduce the number of connections to a microcontroller 44 of the control electronics 12.

The control electronics 12 includes lock-in amplifiers 40 and 41, modulation controllers 42 and 43, the microcontroller 44, an IR laser power supply 46 for providing power to the IR laser 20, a red laser power supply 47 for providing power to the red laser 21, and a DC power supply 48 for providing power to the control electronics 12 and apparatus 10 as a whole. As illustrated, amplifier 40 receives the signal from detector 25 and amplifier 41 receives the signal from detector 26.

The DC power supply 48 is integrated into the enclosure 13 and permits the user to connect a single DC power connection to operate the system. Two connection options are available: a 120V AC plug adapter and a 12V automotive DC adapter. Either can be connected into the power jack to operate the system.

The microcontroller 44 includes the primary processor and performs a number of functions, including:

Take a series of input readings from the RED and IR photodiodes of detectors 25 and 26 and calculate the current average values and the ratio about once per second.

Control the OLED hand held controller 14 and display the current values.

Activate a calibration mode when the calibration button 52 is pressed on the handheld controller 14.

Read and compute the calibration values.

Adjust the gain of the lock-in amplifiers 40, 41 depending on input signal level.

Freeze or resume the display of the handheld controller 14 when the hold button 53 is pressed.

In addition, the software for the microcontroller 44 automatically carries out its functions without user input except to activate the calibration mode and hold or resume live updating of the display. When a calibration is taken, the recorded values are stored in internal EEPROM. When the system is first turned on these values are read back out of EEPROM to retain the previous calibration.

The modulation controllers 42 and 43 are used to control laser modulation. Because maintaining the stability of the laser modulation is important, separate controllers 42 and 43 are used. This is better than simply relying on the microcontroller 44 to maintain the stability. An additional consideration was the need to have an analog output since the particular voltage level for the pulses that modulate the laser has a major effect on the stability and noise in the laser output. The controllers 42 and 43 are used to provide both the analog modulation signal to the lasers as well as the reference TTL signal for the lock-in amplifiers 40 and 41. Since the controllers 42 and 43 cannot output an analog signal directly, a 12-bit Digital to Analog Converter (DAC) was incorporated into the design as part of the microcontroller 44. The DAC is controlled through an I2C interface. Table 2 shows an example list of equipment suitable for use in the control electronics 12.

TABLE 2

| Item | Manufacturer | Part Number | Description |
|---|---|---|---|
| Main Processor | Arduino | Uno | Programmable Atmel Microcontroller |
| Modulation Controllers (x2) | Arduino | Micro | Programmable Atmel Microcontroller |
| Digital-to-Analog Converter | Adafruit | MCP4725 | Small board attached to Arduino |
| Lock-in Amplifier (x2) | Femto | LIA-MV-150-S | Single channel, w/ externally controllable gain |
| Laser Power Supplies | Power Technologies | N/A | Provided by the manufacturer with the lasers |
| OLED Display | Scott Edward Electronics | GLO-416Y | Programmable character size, 4 × 16, serial interface |

The lock-in amplifiers 40 and 41 extract signals with a known frequency from a noisy input signal by mixing a reference input with a detector input to produce a near-DC output signal that is only dependant on the portion of the detector input that is modulated at the reference frequency.

One area of concern was that the signal level required a high dynamic range depending on the distance to the target and the reflectivity of the target surface. The signal digitizer is 10 bits so it can only read values from 0-1023. If only a single gain level was used, then a weak signal (with a value of 50, for example) would be highly susceptible to measurement errors due to system noise. However, by increasing the amplifier gain, and therefore the magnitude of the analog signal, the signal of interest falls within the middle region of the ND input range. As such, the signal of interest is less susceptible to system noise.

The gain can be manually adjusted by turning a knob on the lock-in amplifiers 40 and 41, but as shown, automated approach was used. The lock-in amplifiers 40 and 41 have an input for commanding the gain level to be set externally. These inputs are connected to the microcontroller 44, which is programmed to set the appropriate lines high or low depending on the level of the input signal. Both lock-in amplifiers 40 and 41 must be controlled together to the keep the ratio value correct, so both the IR and RED laser inputs are monitored together to determine when to change levels.

The microcontroller 44 is programmed to use gain levels 4-9, where 4 is the lowest gain (for the strongest signals) and 9 is for highest gain (for the weakest signals). Each gain setting of the lock-in amplifier has a difference of a factor of three from the adjacent settings except for gain 7-8 which are have a difference of a factor of ten. The trade off to higher gain is higher amplifier noise. For gain levels 4-7, the noise is negligible but becomes evident at gain 8 and significant at gain 9. The effect of the noise on the measured ratio is to cause it to fluctuate between measurements with more noise producing more fluctuation. Thus at the highest gains, any single measurement may be suspect, but the average of a number of measurements would be more accurate.

Another area of concern is the presence of ambient light. Ambient light would overwhelm the small reflected signal from the conductors when used in an outdoor environment. Even more significantly, the wavelength ratio of the lasers 20 and 21 would change based on time of day, season, cloud cover and the background behind the conductor. It was found that the ambient effects could be eliminated by modulating the laser source and using the lock-in amplifiers 40 and 41. As a result, only the illumination light is detected and light at all other frequencies, including ambient, is rejected. In addition, it was found that the use of a monochromatic light source eliminates the effects of ambient light on the target conductor and the use of the modulation controllers 42 and 43 and lock-in amplifiers 40 and 41 could be used to modulate the lights and keep the laser outputs from changing.

Initial programming of the apparatus 10 focused on the modulation controllers 42 and 43. It was found that frequencies between 250-400 Hz gave the most stable optical output pulses. It was also found that a frequency of 100 Hz led to a less stable and noisier signal and at frequencies above 700 Hz bandwidth limitations in the laser controller were encountered—driving square wave became rounded off.

The lasers 20 and 21 are modulated using different frequencies so they can be further distinguished by the lock-in amplifiers 40 and 41. The red laser 21 operates at 333 Hz while the infrared laser 20 operates at 286 Hz. The modulation amplitudes were set so as to give the two lasers 20 and 21 a similar average output power. The modulation controllers 42 and 43 are programmed to have a full on and full off mode for the laser in addition to modulation mode for internal calibration purposes.

Figure 4:
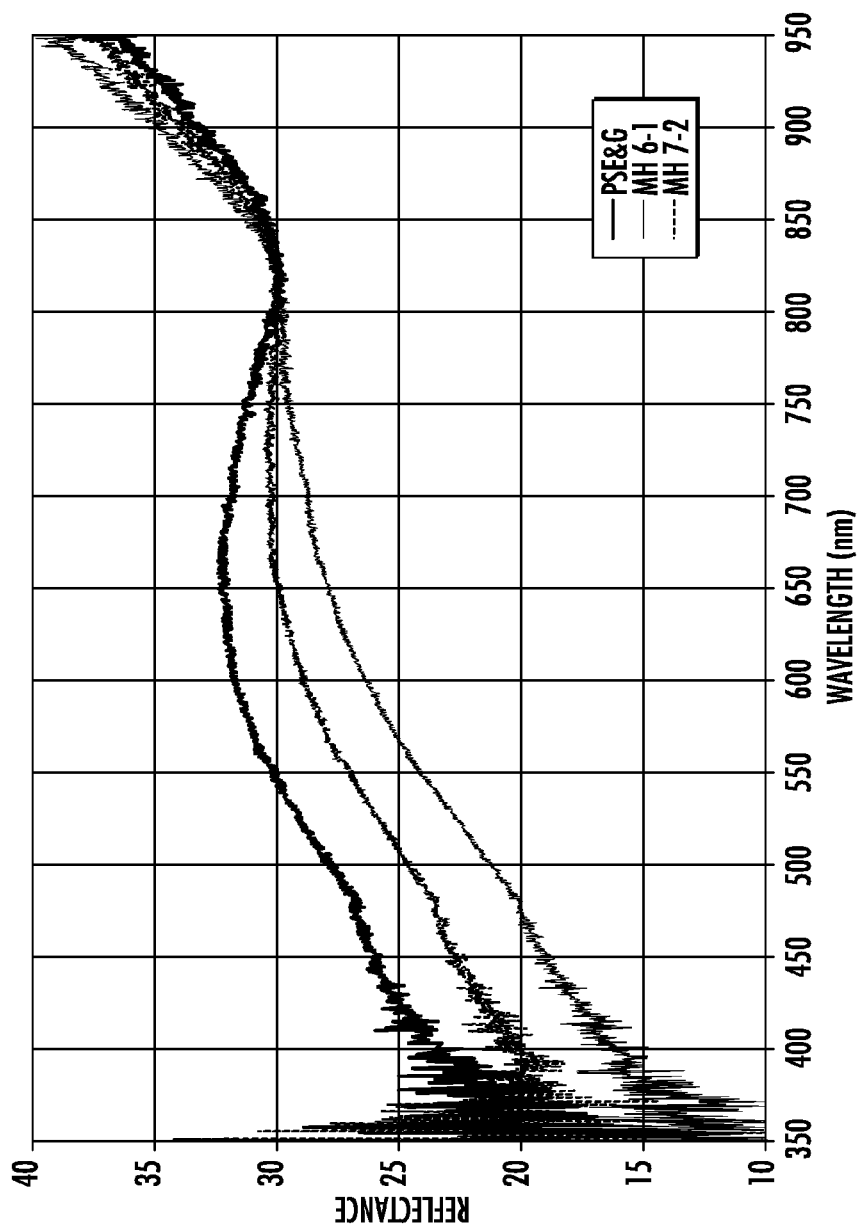
FIG. 4 shows spectral response for oxides.
Figure 5:
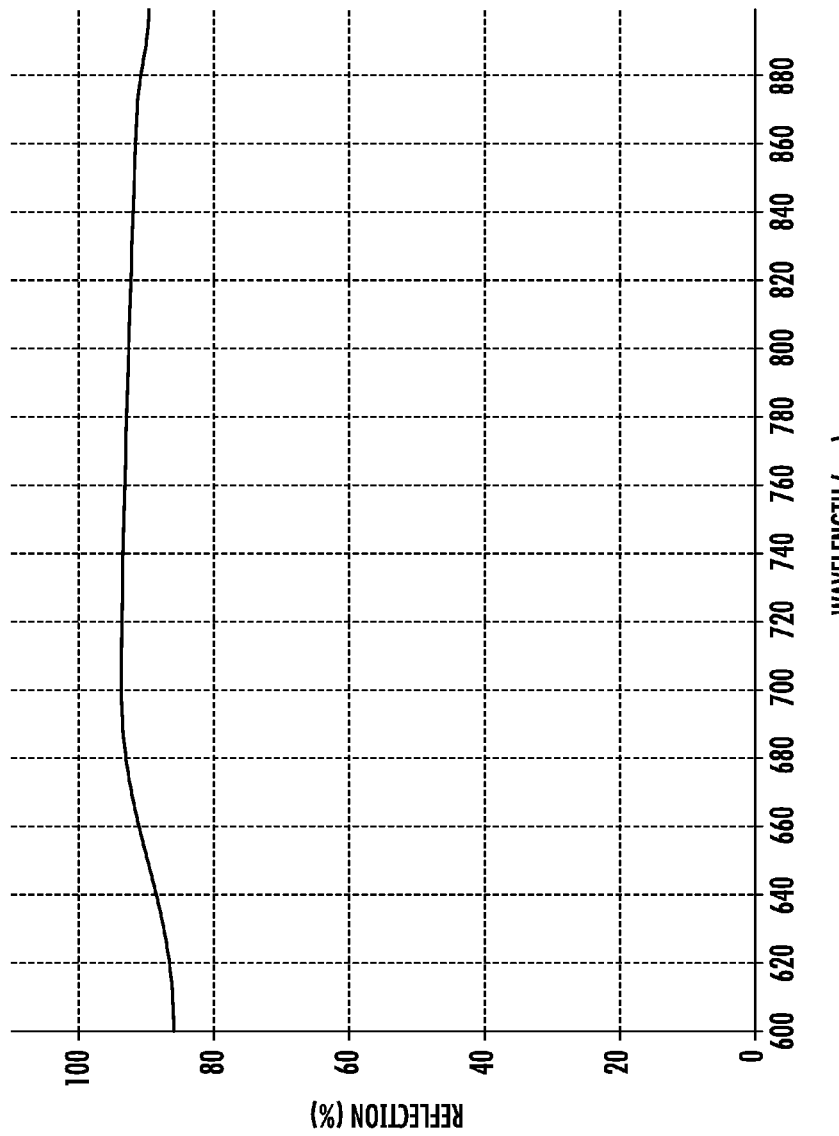
FIG. 5 shows spectral responses of polyvinyl chloride (PVC).

In operation, the apparatus 10 is mounted to a tripod to provide a stable platform and a red dot sighting system 60 is used to allow a user to quickly acquire the target. The apparatus 10 then uses the lasers 20 and 21 to project a light onto the target. The reflected light from the target (an in-service conductor) is captured by the photo detectors 25 and 26 through the telescope 16 and converted into a reflectance value as a function of frequency. Two specific frequencies are then analyzed with the calculation of a ratio based upon the reflectance at 400 nm and 840 nm. This ratio has been correlated with various levels of iron oxide corrosion to confirm the presence of oxides that have leached through the aluminum strands and deposited on the underside of the conductor. FIG. 4 illustrates a spectral response of three sample ACSR conductors in incremental stages of degradation and Table 3 shows typical reference ratios derived from those responses.

TABLE 3

| | RE/IR (668/820) | |
|---|---|---|
| Category | Reflectance Ratio | Std. Deviation |
| New Conductor | 1.01 | N/A (single sample) |
| Light Staining | 0.991 | 0.027 |
| Medium Staining | 0.963 | 0.027 |
| Heavy Staining | 0.940 | 0.021 |
| Medium Pitting* | 1.078 | 0.016 |
| Heavy Pitting | 1.061 | 0.020 |

Several tests were conducted to verify data. Prior to conducting tests on a conductor, the apparatus 10 is calibrated. The calibration is completely automatic after the user presses the calibration button 52—first setting the red laser to full-on and the IR laser off, then the IR laser to full-on and the red laser off. The microcontroller 44 takes readings from the reference photodetector, which is used to calibrate the ratio calculation. This full-on full-off approach avoids the problem of potential instabilities during modulation and eliminates having to demodulate the reference signal to calculate the calibration values.

A white card or plate with a known spectral reflectance is held at a distance in front of the apparatus 10. When the calibration button 52 is pushed, the values for each channel are separately measured using the apparatus's 10 photodetectors 25 and 26 for a few seconds and the values are stored, accounting for the known reflectance of the card or plate. The card or plate is of a PVC material due to the fact that it has a flat spectral response, shown in FIG. 4. The PVC material has a reflectance of 91.1% at 660 nm and 92.1% at 830 nm, the difference of which is accounted for in the calibration code.

A test of the apparatus 10 with several conductors was conducted in the lab at a distance of 90 feet. The conductors were mounted on a stand in front of an absorbing surface to avoid measuring the wall in addition to the conductors. The apparatus 10 was aligned to each conductor in turn, with the conductor centered within the spot. The Red/IR ratio values were recorded along with the actual raw measurement and the amplifier gain. For several of the samples, which had values near the gain 7-8 boundary, measurements were taken with both gain settings to compare. Table 4 contains the measurement data along with data from the white calibration plate and the black background. An additional set of measurements (Table 5) was taken at 60 feet to evaluate the effects of a stronger signal and higher gain.

TABLE 4

| Sample | Ratio | Red value | IR value | Gain | Spectrometer-Ratio* |
|---|---|---|---|---|---|
| MH 8-2 | 0.97 | 86 | 127 | 7 | 0.90 |
| MH 8-2 | 1.06 | 275 | 357 | 8 | 0.90 |
| MH 4-3 | 0.96 | 76 | 113 | 7 | 0.96 |
| MH 4-3 | 1.05 | 267 | 363 | 8 | 0.96 |
| PSE&G | 1.16 | 121 | 152 | 7 | 1.07 |
| PSE&G | 1.27 | 361 | 413 | 8 | 1.07 |
| FE 4 | 1.23 | 128 | 150 | 7 | 1.09 |
| FE 4 | 1.25 | 358 | 413 | 8 | 1.09 |
| CC 2 | 1.23 | 352 | 416 | 7 | 1.13 |
| CC 3 | 1.18 | 384 | 421 | 7 | 1.10 |
| Calibration | — | 624 | 807 | 7 | — |
| Background | — | 43 | 26 | 9 | — |

TABLE 5

| Sample | Ratio | Red value | IR value | Gain | Spectrometer Ratio* |
|---|---|---|---|---|---|
| MH 4-3 | 0.96 | 198 | 304 | 7 | 0.96 |
| FE 4 | 1.18 | 286 | 357 | 7 | 1.09 |
| CC 2 | 1.17 | 275 | 347 | 6 | 1.13 |

An outdoor test was also conducted. The conductor sample was mounted on a tripod stand on a roof of a building and the apparatus 10 at ground level. The total distance was about 160 ft and provided an unobstructed sky background. The test was conducted in the late afternoon so the sun was to the west while the measurement direction was to the east. Sky conditions were mostly clear with occasional clouds passing through the background. The spot size of the laser at this distance was considerably larger than the conductor—about 4" in diameter. Three samples were measured. Table 6 shows the data collected during the test.

TABLE 6

| Sample | Ratio | Red value | IR value | Gain | Spectrometer Ratio* |
|---|---|---|---|---|---|
| MH 8-2 | 0.90 | 115 | 283 | 9 | 0.90 |
| PSE&G | 1.00 | 118 | 211 | 9 | 1.07 |
| CC 2 | 1.32 | 134 | 415 | 8 | 1.13 |
| Calibration | — | 158 | 401 | 7 | — |

The foregoing has described an apparatus and method for evaluating power transmission conductors. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

I claim:

1. An apparatus configured to evaluate a charged power transmission conductor at a distance, comprising:
    (a) a telescope assembly configured to transmit light to the conductor and receive a reflected light, in response to the transmitted light, from the conductor, the telescope assembly including:
        (i) an infra-red laser and a red laser configured to transmit light at a first, infra-red frequency and a second, red frequency, respectively, through a collimating output lens to the conductor;
        (ii) a telescope configured to receive the reflected light;
        (iii) a dichroic splitter configured to split the reflected light received by the telescope into first and second light signals at the first and second frequencies;
        (iv) first and second photodetectors configured to receive the first and second light signals, respectively; and
    (b) control electronics connected to the telescope assembly and configured to analyze the reflected light and determine a ratio of reflectance of the first frequency to the second frequency, wherein the ratio is correlated with levels of iron oxide corrosion to confirm the presence of oxides that have leached through strands of the conductor, the control electronics including:
        (i) first and second lock-in amplifiers configured to produce a near DC output signal, the first lock-in amplifier being connected to the first photodetector and the second lock-in amplifier being connected to the second photodetector;
        (ii) first and second modulation controllers configured to modulate the infra-red and red lasers, the first modulation controller being connected to the infra-red laser and the second modulation controller being connected to the red laser; and
        (iii) a microprocessor connected to the first and second lock-in amplifiers and the first and second modulation controllers, the microprocessor configured to control the apparatus and perform processing of the reflected light.

2. The apparatus according to claim 1, further including a handheld controller connected to the microprocessor, the handheld controller configured to activate a calibration mode of the apparatus and to provide conductor test information to a user.

3. The apparatus according to claim 2, wherein the handheld controller includes a visual display to provide test information to the user.

4. A method of evaluating a charged power transmission conductor, comprising the steps of:
    (a) providing an apparatus, comprising:
        (i) a telescope assembly; and
        (ii) control electronics;
    (b) aiming the telescope assembly at a conductor to be evaluated;
    (c) transmitting light from a first laser at a first, infra-red frequency and a second laser red laser at a second, red frequency through a collimating output lens mounted in front of the telescope assembly and then to the conductor;

(d) using the telescope assembly to receive a reflected light signal from the conductor;

(e) splitting the reflected light signal into two reflected light signals at the first and second frequencies;

(f) using the control electronics to process the reflected light signals and determine a ratio of reflectance of the first frequency to the second frequency that is correlated with levels of iron oxide corrosion to confirm the presence of oxides that have leached through strands of the conductor.

5. The method according to claim 4, further including the step of using a red dot sight to aim the telescope assembly at the conductor.

6. The method according to claim 4, further including the step of outputting the ratio to a visual display on a handheld controller.

7. The method according to claim 4, further including the step of splitting the reflected light signal into two reflected light signals at pre-determined frequencies.

\* \* \* \* \*